(12) United States Patent
Dugar et al.

(10) Patent No.: US 6,630,506 B1
(45) Date of Patent: Oct. 7, 2003

(54) BICYCLIC ACYL GUANIDINE SODIUM/PROTON EXCHANGE INHIBITORS AND METHOD

(75) Inventors: Sundeep Dugar, San Jose, CA (US); Steven V. O'Neil, Lawrenceville, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 392 days.

(21) Appl. No.: 09/556,739

(22) Filed: Apr. 21, 2000

Related U.S. Application Data

(60) Provisional application No. 60/137,326, filed on Jun. 3, 1999, and provisional application No. 60/130,667, filed on Apr. 23, 1999.

(51) Int. Cl.[7] .................. C07D 215/54; A61K 31/55
(52) U.S. Cl. .................. 514/432; 514/450; 514/456; 548/131; 548/128; 548/236; 548/247; 548/364.4; 549/23; 549/402; 549/405
(58) Field of Search .................. 549/23, 355, 405, 549/402; 514/432, 450, 456

(56) References Cited

U.S. PATENT DOCUMENTS

| | | | |
|---|---|---|---|
| 3,728,332 A | 4/1973 | Tessler et al. | |
| 5,336,689 A | 8/1994 | Weber et al. | |
| 5,561,146 A | 10/1996 | Kim et al. | |
| 5,733,934 A | 3/1998 | Ramakrishna et al. | |
| 5,756,535 A | 5/1998 | Schwark et al. | |
| 5,814,654 A | 9/1998 | Kitano et al. | |
| 5,852,046 A | 12/1998 | Lang et al. | |
| 5,977,100 A | 11/1999 | Kitano et al. | |
| 6,011,059 A | 1/2000 | Ahmad et al. | |
| 6,346,527 B1 * | 2/2002 | Takenaka et al. | 514/213.01 |
| 6,369,110 B1 * | 4/2002 | Kitano et al. | 514/617 |

FOREIGN PATENT DOCUMENTS

| | | | |
|---|---|---|---|
| EP | 0622356 B1 | 11/1994 | |
| EP | 0639573 A1 | 2/1995 | |
| EP | 0738712 B1 | 10/1996 | |
| EP | 0744397 A1 | 11/1996 | |
| EP | 0790245 A1 | 8/1997 | |
| EP | 0803501 A1 | 10/1997 | |
| JP | 07010839 | 1/1995 | |
| JP | 853336 | 2/1996 | |
| JP | 09059245 | 3/1997 | |
| JP | 09067340 | 3/1997 | |
| JP | 10237073 | 9/1998 | |
| JP | 10316647 | 12/1998 | |
| WO | WO 9604241 A2 | 2/1996 | |
| WO | WO 97/46226 | 12/1997 | |
| WO | WO 98/55475 | 12/1998 | |
| WO | WO99/55690 | 11/1999 | |
| WO | 9961414 | * 12/1999 | 549/350 |

OTHER PUBLICATIONS

Dialog Abstract of JP 9067340; Yamanouchi Pharm. (1995).
Dialog Abstract of JP 9059245; Yamanouchi Pharm. (1995).
Dialog Abstract of JP 10237073; Sumitomo Pharm. (1997).
Dialog Abstract of JP 7010839, Sumitomo Phar. (1994).
Derwent Abstract of JP 8053336, Shiseido Co. Ltd (1996).
Derwent Abstract of JP 10316647, Fujisawa Pharm. Co. Ltd. (1998).

* cited by examiner

*Primary Examiner*—Robert Gerstl
(74) *Attorney, Agent, or Firm*—Ronald S. Hermenau; Stephen B. Davis

(57) ABSTRACT

Acyl guanidines are provided which are sodium/proton exchange (NHE) inhibitors which have the structure

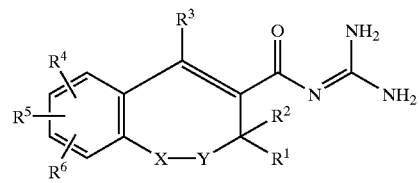

wherein n is 0 to 4; X is a bond, O, S, SO, $SO_2$, CO,

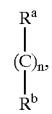

or $NR^7$; Y is a bond, O, S, SO, $SO_2$, CO,

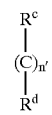

or $NR^{7'}$ wherein at least one of X and Y is other than a bond; and $R^1$, $R^2$, $R^3$, $R^4$, $R^5$, $R^6$, $R^7$ and $R^a$, $R^b$, $R^c$, $R^d$ are as defined herein, and are useful as antianginal, cardioprotective agents, antiischemic agents, and agents for peripheral vascular disease including intermittent claudication. In addition, a method is provided for preventing or treating angina pectoris, cardiac dysfunction, myocardial necrosis, arrhythmia, peripheral vascular diseases (PVD), including peripheral atherosclerotic disease (PAD), including intermittent claudication, Raynaud's diseases, and LeRiches Syndrome, pain, parethesia or discomfort in the lower limb and gluteal regions produced by vascular (e.g. arterial) insufficiency (where symptoms are initiated or worsened with ambulation), employing the above acyl guanidines.

26 Claims, No Drawings

BICYCLIC ACYL GUANIDINE SODIUM/PROTON EXCHANGE INHIBITORS AND METHOD

This application claims priority from provisional U.S. application Serial No. 60/137,326 filed Jun. 3, 1999 and from provisional U.S. application Serial No. 60/130,667 filed Apr. 23, 1999, the entirety of which applications is incorporated herein by reference.

FIELD OF THE INVENTION

The present invention relates to bicyclic acyl guanidine compounds which are sodium/proton exchange (NHE) inhibitors and are useful as antianginal agents, and cardioprotective agents and for treating peripheral vascular disease including intermittent claudication.

BRIEF DESCRIPTION OF THE INVENTION

In accordance with the present invention, novel bicyclic acyl guanidines are provided which are sodium/proton exchange (NHE) inhibitors and have the structure I

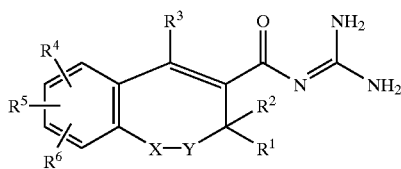

including pharmaceutically acceptable salts thereof, all stereoisomers thereof, and prodrug esters thereof,
wherein
$R^1$ and $R^2$ are the same or different and are independently H, alkyl, alkenyl, alkynyl, alkoxy, alkenyloxy, alkynyloxy, (alkyl or aryl)$_3$Si (where each alkyl or aryl group is independent), cycloalkyl, cycloalkenyl, aryl, arylalkyl, aryloxy, cycloheteroalkyl, cycloheteroalkylalkyl, heteroaryl, heteroaryloxy, arylthio, arylsulfinyl, arylsulfonyl, thio, alkylthio, alkylsulfinyl, alkylsulfonyl, heteroarylthio, heteroarylsulfinyl, hetero-arylsulfonyl, halogen, haloalkyl, polyhaloalkyl such as $CF_3$ and $CF_3CH_2$, polyhaloalkyloxy such as $CF_3O$ and $CF_3CH_2O$, alkylaminocarbonyl, arylaminocarbonyl, heteroarylaminocarbonyl, acyl, carboxy, aminocarbonyl, alkylcarbonyl, alkoxycarbonyl, arylcarbonyl, heteroarylcarbonyl, cyano, tetrazolyl, imidazole, oxazole or triazole, —PO($R^8$) ($R^9$), S(O)$_2R^8$, $R^9$ (where $R^1$ and $R^9$ are the same or different and are independently hydrogen, alkyl, aryl, alkoxy, aryloxy, cycloalkyl, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy);

Additionally $R^1$ and $R^2$ can be optionally joined together to form a non-aromatic substituted or unsubstituted carbocyclic ring (namely, a cycloalkyl or cycloalkenyl ring), or a cycloheteroalkyl ring (which includes one, two or three hetero atoms such as O, S and/or N), which ring contains 3 to 8 members.

X is a bond, O, S, SO, SO$_2$, CO,

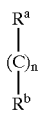

or NR$^7$ (wherein R$^7$ is H, lower alkyl, alkanoyl, or —SO$_2$alkyl);
Y is a bond, O, S, SO, SO$_2$, CO,

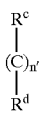

or NR$^{7'}$ (wherein R$^{7'}$ is H, lower alkyl, alkanoyl, or SO$_2$alkyl);
n is an integer from 1 to 4;
n' is an integer from 1 to 4; with the proviso that at least one of X and Y is other than a bond;
$R^a$, $R^b$, $R^c$ and $R^d$ may be the same or different and are any of the groups set out under the definition of $R^1$ and $R^2$, and may be the same as or different from $R^1$ or $R^2$;
where n is >1 and/or n'>1, then in the repeating

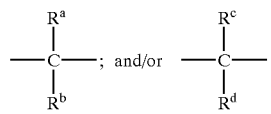

groups, $R^a$ and $R^b$ in repeating groups may be the same of different, and $R^c$ and $R^d$ in repeating groups may be the same or different.
$R^3$, $R^4$, $R^5$ and $R^6$ are the same or different and are independently selected from H, alkyl, alkenyl, alkynyl, alkoxy, alkenyloxy, alkynyloxy, (alkyl or aryl)$_3$Si (where each alkyl or aryl group is independent), cycloalkyl, cycloalkenyl, aryl, arylalkyl, aryloxy, cycloheteroalkyl, cycloheteroalkylalkyl, heteroaryl, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl such as $CF_3$ and $CF_3CH_2$, polyhaloalkyloxy such as $CF_3O$ and $CF_3CH_2O$, acyl, carboxy, aminocarbonyl, alkylcarbonyl, alkoxycarbonyl, arylcarbonyl, heteroarylcarbonyl, cyano, tetrazolyl, imidazole, oxazole or triazole, —PO($R^{12}$) ($R^{13}$), S(O)$_2R^{12}$, $R^{13}$ (where $R^{12}$ and $R^{13}$ are the same or different and are independently hydrogen, alkyl, aryl, alkoxy, aryloxy, cycloalkyl, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy), amino, alkylamino, alkenylamino, alkynylamino, arylalkylamino, arylamino, heteroarylamino, thio, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, alkylcarbonyloxy, alkylcarbonylamino, arylcarbonyloxy, arylcarbonylamino, heteroarylcarbonyloxy, heteroarylcarbonylamino, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, 1,1-(alkoxyl or aryloxy)$_2$alkyl (where the two aryl or alkyl substituents can be independently defined, or linked to one another to form a ring, such as 1,3-dioxane or 1,3-dioxolane), —NR$^{10}$(C=NR$^{11}$)alkyl, —NR$^{10}$(C=NR$^{11}$)alkenyl, —NR$^{10}$(C=NR$^{11}$)alkynyl, —NR$^{10}$(C=NR$^{11}$)heteroaryl, or —NR$^{10}$(C=NCN)-amino;

$R^{10}$ and $R^{11}$ are the same or different and are independently hydrogen, alkyl, haloalkyl, aryl, alkoxy, aryloxy, cycloalkyl, heteroaryl, arylalkyl, or cycloheteroalkyl.

Additionally any two adjacent $R^4$, $R^5$ and $R^6$ substituents can be joined together to form an aromatic or non-aromatic, substituted or unsubstituted ring (such as a cycloalkyl or cycloalkenyl ring), a cycloheteroalkyl ring or a heteroaryl ring, which ring contains 5 to 8 members.

Preferred are compounds of formula I of the invention wherein Y is a bond; that is

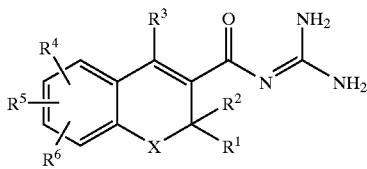

Preferably X is O or S; more preferably, X is O; preferably $R^1$ and $R^2$ are the same or different and are independently hydrogen, lower alkyl, perhaloalkyl, halogen, lower alkoxy, or aryl, at least one of $R^1$ and $R^2$ being other than hydrogen; more preferably $R^1$ and $R^2$ are the same or different and are independently hydrogen, lower alkyl, or perhaloalkyl, and $R^3$ is H; preferably $R^4$, $R^5$ and $R^6$ are the same or different and are independently H, lower alkyl, lower alkoxy, aryl, perhaloalkyl, or halogen; more preferably $R^4$, $R^5$ and $R^6$ are the same or different and are independently hydrogen, lower alkyl, lower alkoxy or halogen.

Preferred examples of $R^1$ and $R^2$ groups include methyl, ethyl, isopropyl, t-butyl, trifluoromethyl or phenyl. Preferred examples of $R^4$, $R^5$ and $R^6$ groups include fluoro, chloro, methyl, trifluoromethyl or methoxy.

In addition, in accordance with the present invention, methods for preventing, inhibiting or treating angina (stable or unstable), cardiac dysfunction, myocardial necrosis, arrhythmia, peripheral vascular disease including intermittent claudication are provided, wherein a compound of formula I of the invention is administered in a therapeutically effective amount which inhibits sodium/proton exchange.

In addition, a method is provided for the relief of symptoms of pain, parethesia or discomfort in the lower limb and gluteal regions produced by arterial insufficiency where symptoms are initiated or worsened with ambulation, which includes the step of administering to a mammalian species in need of treatment a therapeutically effective amount of a compound of formula I.

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain,such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various additional branched chain isomers thereof, and the like as well as such groups including 1 to 4 substituents which may be halo, for example F, Br, Cl or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, nitro, cyano, haloalkyl, polyhaloalkyl (or perhaloalkyl) and/or alkylthio and/or any of the $R^1$ groups.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to one aromatic ring as described for aryl; examples include cyclopropyl, cyclobutyl, cyclopentyl, cyclohexyl, cycloheptyl, cyclooctyl, cyclodecyl and cyclododecyl, cyclohexenyl,

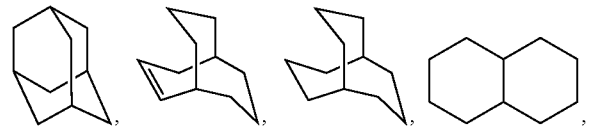

any of which groups may be optionally substituted with 1 to 4 substituents which may be any of the substituents set out for alkyl.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, or 3 groups selected from hydrogen, halo, haloalkyl, alkyl, polyhaloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfon-aminocarbonyl, or any of the substituents set out for alkyl.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be independently substituted with one or two substituents (substituted amino), which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio or any of the substituents for alkyl.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_p$ (where p is 1 to 8, preferably 1 to 5) (which may include alkylene, alkenylene or alkynylene groups) as defined herein, may optionally include 1, 2, or 3 substituents which include any of the substituents for alkyl.

Examples of alkylene, alkenylene and alkynylene include

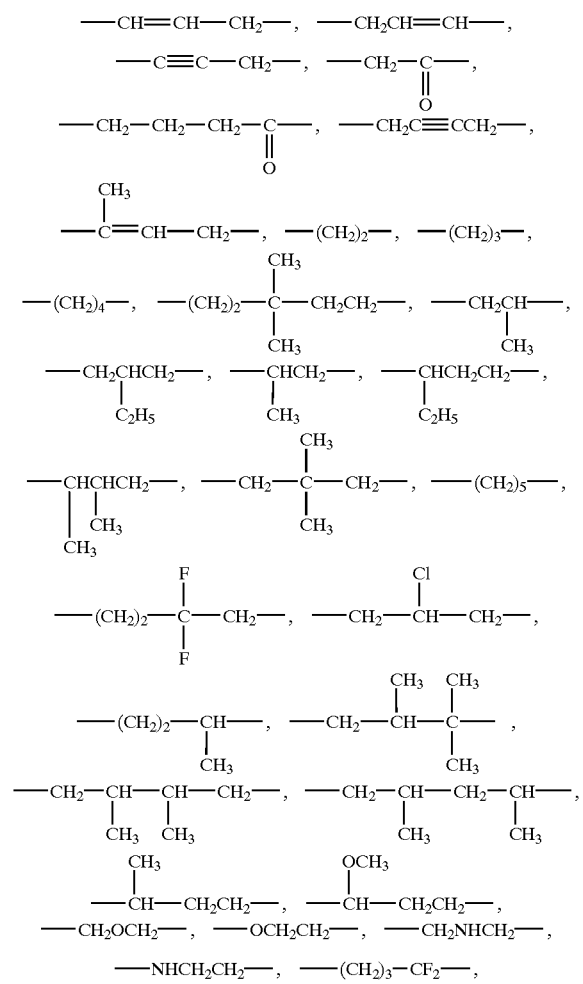

-continued

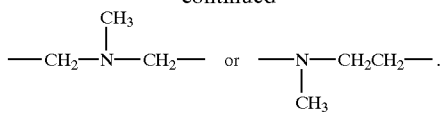

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

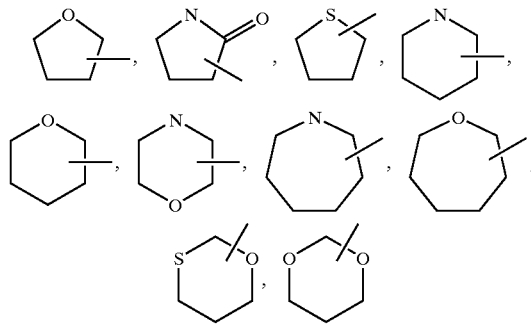

and the like. The above groups may include 1 to 4 substituents such as alkyl, halo, oxo and/or any of of the substituents for alkyl. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents for alkyl. Examples of heteroaryl groups include the following:

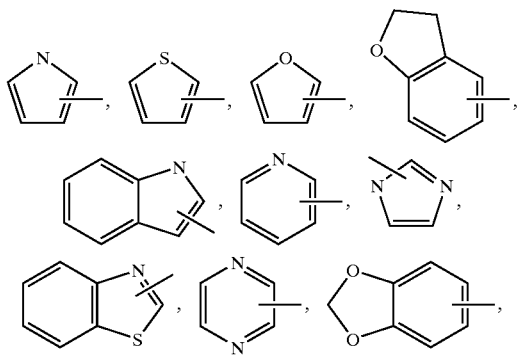

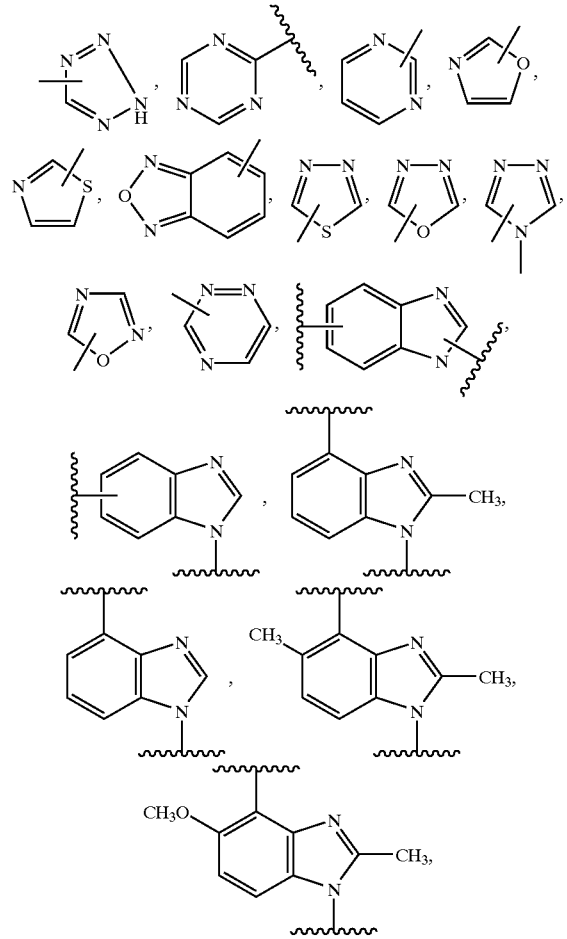

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" or "perhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$)-alkyl- or aryl-sulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate, nitrate or maleate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

It should be understood that the present invention includes prodrug forms of the compounds of formula I such as alkylesters of acids or any of the prodrugs for guanidines disclosed in U.S. application Ser. No. 08/641,718, filed May 2, 1996, and in U.S. Pat. No. 5,561,146 which are incorporated herein by reference.

The compounds of the instant invention may, for example, be in the free or hydrate form, and may be obtained by methods exemplified by the following descriptions.

The compounds of formula I may be prepared by the preferred processes described in the following reaction schemes. Exemplary reagents and procedures for these reactions appear hereinafter and in the working Examples.

Compounds of formula I of the invention can be prepared from the corresponding carboxylic acids by using the sequence of steps outlined in Scheme 1 set out below. Activation of carboxylic acid 1 with various activating reagents (e.g. 1,1'-carbonyldiimidazole (CDI), thionyl chloride, oxalyl chloride, and the like) (employing a molar ratio of activating agent:acid 1 within the range from about 1:1 to about 10:1) in an organic solvent such as THF or methylene chloride, convert acids 1 to 2. Subsequent treatment of compounds of formula 2 with guanidine in DMF or THF (employing a molar ratio of guanidine:2 within the range from about 1:1 to about 20:1) gives compounds of the formula I.

The carboxylic acids of formula 1 can either be commercially available or they can be prepared by methods known in the art or via the routes shown in Schemes 2, 3, 4, 5, 6 and 7.

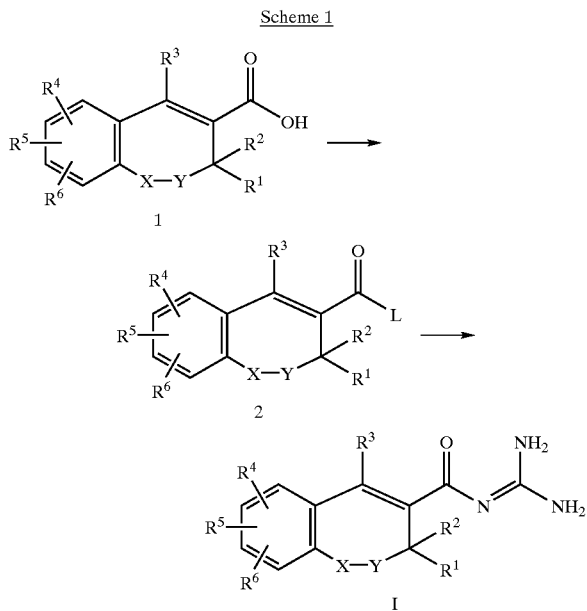

Scheme 1

(L=a leaving group such as halide, alkoxy, aryloxy or imidazolyl).

Compounds of formula IA of the invention where X is O, Y is a bond, and $R^2$ is H can be prepared as shown in Scheme 2.

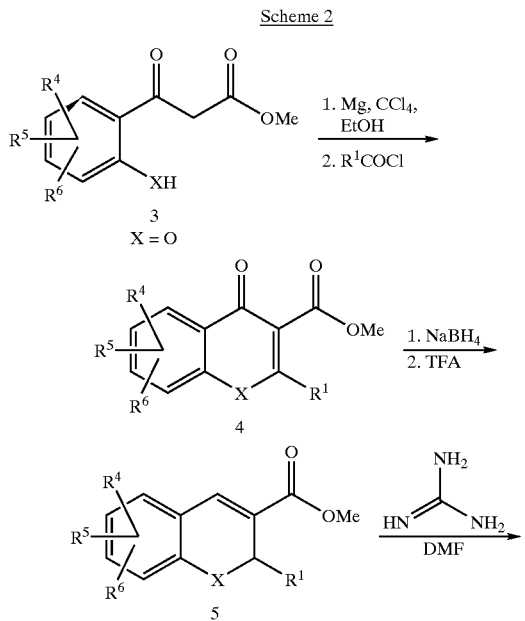

Scheme 2

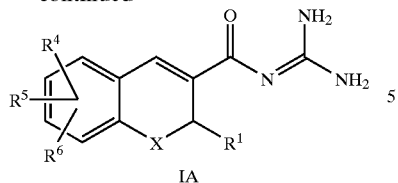

The esters a used in this preparation are either commercially available or they can be prepared by methods known to those skilled in the art. Thus, condensation of esters 3 with the acid chlorides gives 4 which upon reduction and elimination yields esters 5. Treatment of esters 5 with guanidine in an appropriate solvent such as dimethylformamide gives the desired compounds IA of the invention.

Compounds of formula IB of the invention wherein X is O or S, Y is a bond and $R^2$ and $R^3$ are other than H can be prepared as shown in Scheme 3.

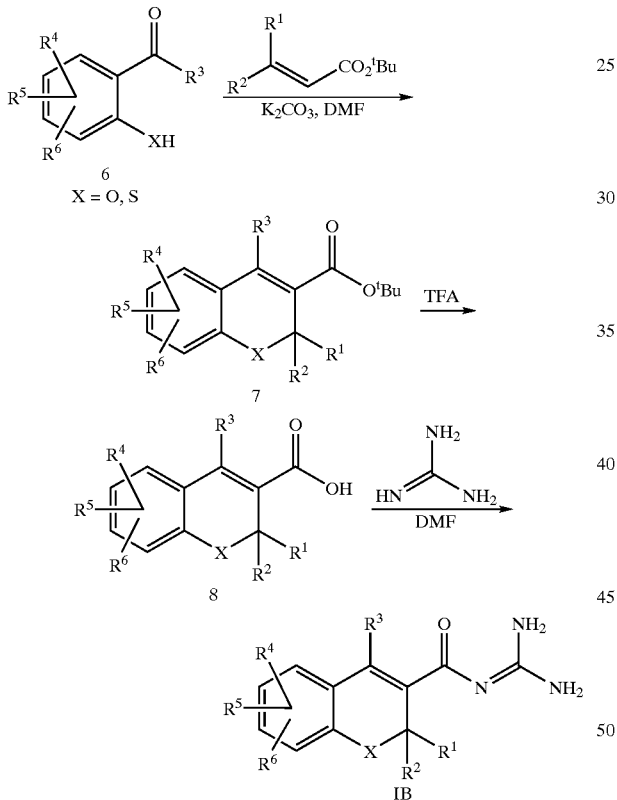

The starting aldehydes 6 are either commercially available or they can be prepared by methods well known to those skilled in the art. Compound 6 is treated with the appropriate acrylic acid ester in the presence of a base such as potassium carbonate to provide a compound of formula 7. Compound 7 is converted to the desired product IB of the invention by deprotection of the acid under appropriate conditions followed by coupling of the resulting acid 8 with guanidine (employing a molar ratio of guanidine:8 within the range from about 1:1 to about 20:1) utilizing a coupling agent such as 1,1'-carbonyldiimidazole.

Compounds of formula IC of the invention wherein X=O or S, Y is

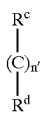

can be prepared according to Scheme 4.

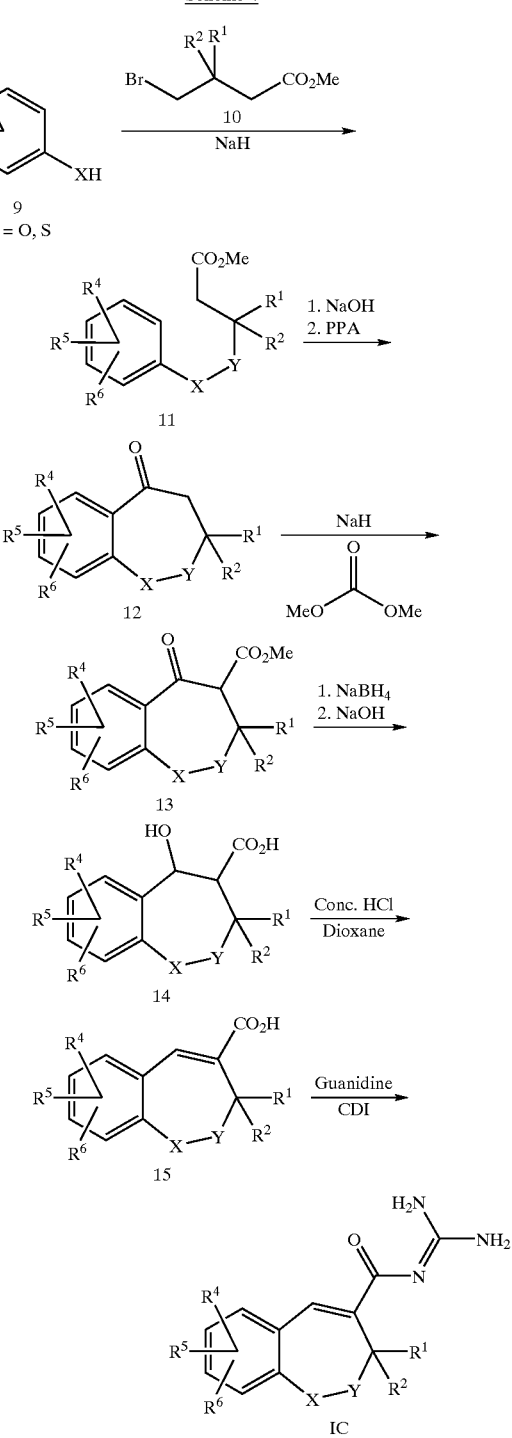

The reaction of 9 with 10 in the presence of a base (such as sodium hydride) gives compound of formula 11 which can be converted to the ketone 12 after hydrolysis of the ester and cyclization of the resulting acid. 12 can then be converted to 11 by the carbonylation of the ketone with an agent such as dimethylcarbonate in the presence of a base such as sodium hydride. Compound 15 can be made from 13 by the reduction of the ketone with a reducing agent such as sodium borohydride and hydrolysis of the ester to give 14 which upon treatment with a strong acid such as hydrochloric acid yields 15. The desired compounds of formula 1C of the invention can then be obtained by reacting the acids 15 with guanidine as described in Scheme 2. Compounds of formula 9 are commercially available or they can be prepared by methods described in the literature.

Compounds of formula I of the invention where X is S can be oxidized to the corresponding sulfoxide or sulfone employing oxidizing agents known in the literature, such as m-chloroperbenzoic acid or oxone.

The compounds of formula IA of the invention where X=O or S, and Y is a bond can also be prepared as in Scheme 5.

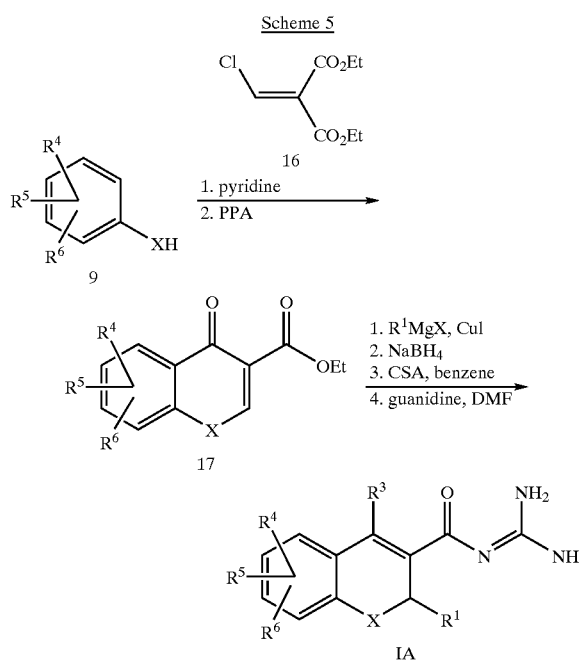

Scheme 5

The starting phenols or thiols 9 are either commercially available or they can be prepared by methods well known to those skilled in the art. Compound of formula 9 is treated with the diester 16 in the presence of a base such as pyridine. The product of this reaction is then treated with an acid such as polyphosphoric acid (PPA) to provide a compound of formula 17. Compound 17 is converted to the desired product IA in a four step sequence by first treatment with an appropriate organometallic reagent $R^1MgX$, followed by reduction with a reducing agent such as sodium borohydride, treatment of this with an acid such as camphorsulfonic acid in a solvent such as benzene with the azeotropic removal of water followed by treatment of the product with guanidine in an appropriate solvent such as dimethylformamide.

The compounds of formula IA were X=NR$^7$, Y is a bond, and $R^2$ is H and $R^1$ is other than H, can be prepared as in Scheme 6.

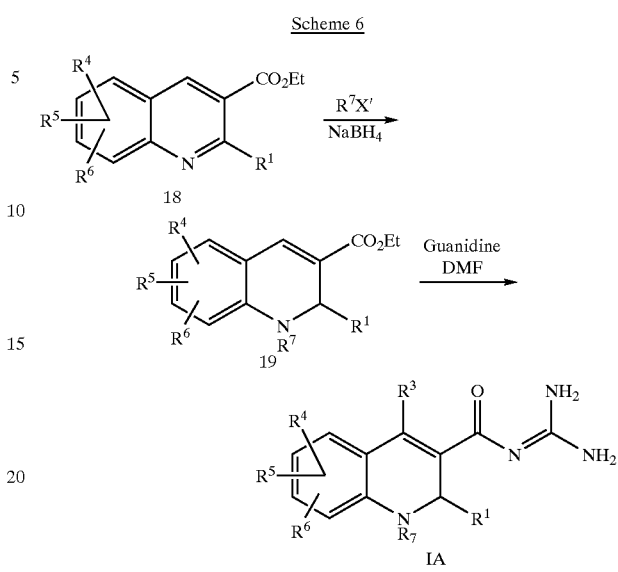

X' = Cl or Br

The starting isoquinolines 18 are either commercially available or they can be prepared by methods well known to those skilled in the art. Compound of formula 18 is treated with an appropriate alkylating or acylating reagent $R^7X'$, followed by the treatment of a reducing agent such as sodium borohydride to give 19 which is then converted to 1A with guanidine in an appropriate solvent such as dimethylformamide.

The compounds of formula IB (where X=NR$^7$ and $R^1 \neq H$ and Y is a bond) may also be prepared as in Scheme 7.

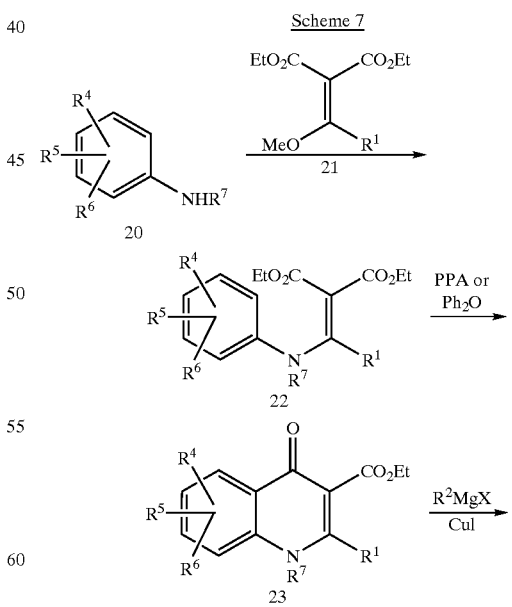

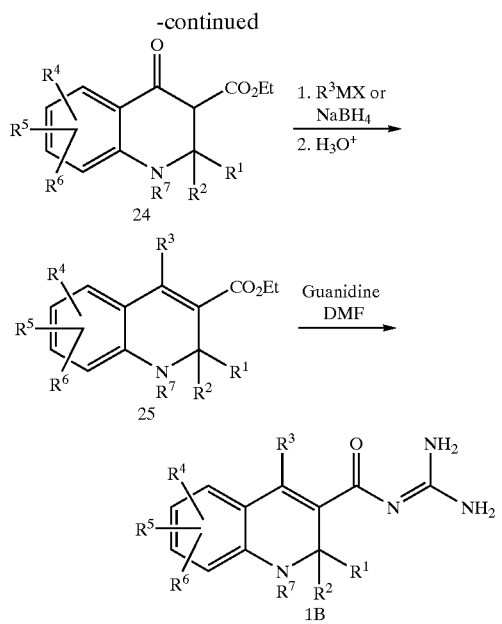

The starting anilines 20 are either commercially available or they can be prepared by methods well known to those skilled in the art. Compound of formula 20 can be treated with compounds of formula 21 to give 22. 22 may be cyclized to 23 using an appropriate reagent such as polyphosphoric acid or diphenylether. 23 may be further alkylated with an appropriate organometallic agent in the presence of a catalyst such as copper iodide to give 24. 24 may be treated with a reducing agent such as sodium borohydride followed by an acid such as hydrochloric acid to give 25 which is then converted to 1B with guanidine in an appropriate solvent such as dimethylformamide.

The compounds of formula I of the invention exhibit Na+/H+ exchange inhibitory activity, and hence, are useful for treating or preventing disorders caused by intracellular acidosis during myocardial ischemia, such as cardiac dysfunction, myocardial necrosis, arrhythmia, reperfusion injury, and the like which are observed in ischemic heart diseases (e.g., myocardial infarction and angina pectoris).

Thus, compounds of formula I of the invention may be used as antiischemic agents, i.e., for the treatment of ischemic conditions including acute and chronic ischemic conditions such as myocardial ischemia, cerebral ischemia, peripheral vascular diseases or disorders including lower limb ischemia peripheral atherosclerotic disease, tissue ischemia and intermittent claudication, LeRiches Syndrome and Raynaud's disease. Thus, a composition containing one (or a combination) of the compounds of this invention, may be administered to a species of mammal (e.g., humans, dogs or cats) suffering from an ischemic condition or any of the conditions set out above.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the Na+/H+ exchange inhibiting and antiischemic activity of the compounds of this invention, these compounds are also useful in the treatment of cardiovascular disorders. For example, compounds of the present invention are useful as therapy for congestive heart failure, intermittent claudication and therapy for hypertension, as antianginal agents, as antifibrillatory agents, and in limiting myocardial infarction.

Compounds of the present invention are additionally expected to be useful in the treatment of cerebral ischemia (e.g., stroke).

As a result of the Na/H exchange inhibiting activity, the compounds of this invention can also be used for the treatment of diseases associated with proliferation of smooth muscle cells, mesangial cells, and fibroblasts. Such diseases include restenosis after angioplasty, renal fibrosis, atherosclerosis, hepatic fibrosis, prostate hypertrophy, pulmonary fibrosis and glomerular nephrosclerosis.

Other uses for compounds of this invention which inhibit Na/H exchange and ischemia include treatments for diseases such as cardiac hypertrophy, ischemic/reperfusion injury associated with organ transplantation, and other surgical procedures such as percutaneous transluminal coronary angioplasty (PTCA).

Due to their Na/H exchange inhibiting and antiischemic properties, compounds of this invention can also be used for CNS disorders associated with cerebral ischemia such as cerebral infarction, cerebral edema and like. Additionally, they can be used for ischemia and ischemia-reperfusion injury resulting from shock and trauma.

The compounds of the invention are also anti-thrombotic agents and antiproliferative agents and are also useful in treating renal disease.

The compounds of the invention are also dual inhibitors of NHE-1 and NHE-3 and thus can be used as cardioprotectants for the treatment of heart disease, whilst also improving renal function by protecting against renal damage, or reversing hypertension by a direct modulation of sodium resorbtion in the kidney. As dual inhibitors, the compounds of the invention are also useful in a combination of therapies, for example, hypertension in patients with acute coronary syndromes, MI, recovery from MI and chronic stable angina. They are also useful for heart failure when an anti-hypertensive or diuretic agent is required for treatment.

Compounds of this invention can be additionally used for the treatment of diabetes mellitus and other diabetic complications and for lowering serum lipids such as lowering LDL-cholesterol.

The compounds of this invention can also be formulated in combination with a diuretic such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as verapamil, nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are of preferred embodiments of the invention. It should be understood that there may be other embodiments which fall within the spirit and scope of the invention as defined by the claims appended hereto.

EXAMPLE 1

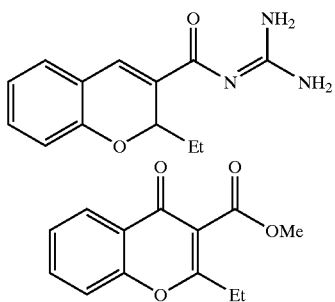

A

A solution containing methyl salicylacetate (1.55 g, 8.0 mmol), magnesium (0.19 g, 8.0 mg-atom), and CCl$_4$ (10 drops) in EtOH (50 mL) was heated at 50–55° C. until all of the magnesium dissolved (6 h). The solvent was then removed at reduced pressure and a solution of propionyl chloride (170 mg, 1.84 mmol) in benzene (100 mL) was added. This solution was heated at reflux for 6 h, cooled to rt, treated with 80 mL of 10% aqueous acetic acid, and extracted with CH$_2$Cl$_2$. The combined organic extracts were washed with brine and dried over Na$_2$SO$_4$. Flash chromatography of the crude residue remaining after concentration at reduced pressure gave 1.1 g of the desired compound (59% yield); MS 233 (M+1).

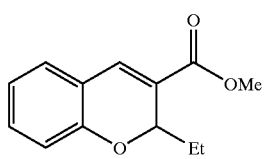

B

A solution of Part A intermediate (500 mg) in MeOH was treated with NaBH$_4$ portionwise until none of the starting compound could be detected by TLC. The reaction was diluted with ether, washed with 1 N HCl and brine, dried (MgSO$_4$), and concentrated at reduced pressure. The crude residue was dissolved in 5 mL of TFA and stirred at rt for 2 h. Removal of the TFA at reduced pressure followed by flash chromatography on silica gel gave the desired product (205 mg, 46% yield); MS 219 (M+1).

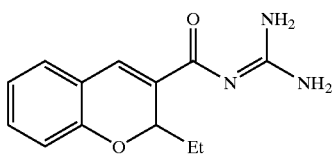

C

Intermediate from Part B (122 mg, 0.59 mmol) was taken up in dimethylformamide (5 mL) and treated with 5 eq of guanidine (180 mg, 3 mmol). The solution was stirred at rt overnight, concentrated at reduced pressure, and purified by preperative HPLC to yield the desired product as the trifluoroacetic acid salt.

$^1$H NMR (400 MHz, DMSO-d$_6$) 8.73 (br s, 2), 8.41 (br s, 2), 7.66 (s, 1), 7.36 (dd, 1, J=8.1, 7.3), 7.32 (d, 1, J=7.5), 7.12 (s, 1), 7.02 (dd, 1, J=7.5, 7.3), 6.95 (d, 1, J=8.1), 5.10 (dd, 1, J=9.2, 3.7), 1.65 (m, 1), 1.56 (m, 1), 0.93 (t, 3, J=7.3); MS 246 (M+1).

Examples 2–5 were prepared following the method described in Example 1.

| Example | Structure | Characterization (MS) |
|---|---|---|
| 2 | 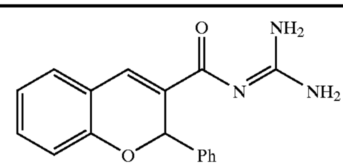 | (M+H) $^+$294 |
| 3 | 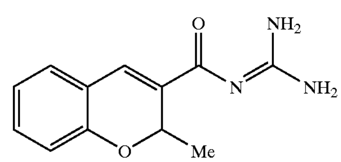 | (M+H) $^+$232 |
| 4 | 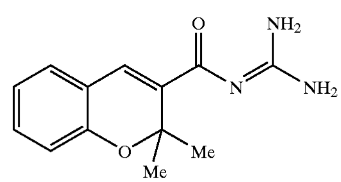 | (M+H) $^+$246 |
| 5 | 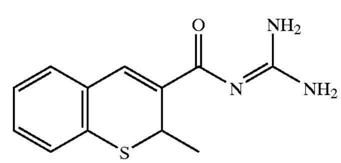 | (M+H) $^+$248 |

EXAMPLE 6

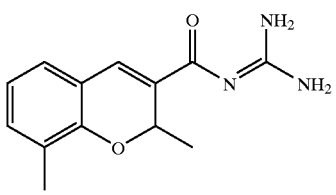

A

-continued

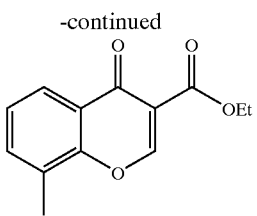

O-Cresol (1.08 g, 10.0 mmol) was treated with diethyl (chloromethylene)malonate (1.03 g, 5.0 mmol) in pyridine (0.6 mL) at rt for 12 h. The solution was diluted with ether, washed with 1 N HCl, 1 M NaOH, and brine, dried (MgSO$_4$), and concentrated under reduced pressure to yield 1.4 g (100%) of the coupled adduct. A polyphosphoric acid ring closure was carried out on the crude material as described in the literature (Ref: Hormi, O. E., Moisio, M. R., Sund, B. C. *J. Org. Chem.* 1987, 52, 5272.) to yield 470 mg (36%) of the desired product after purification by flash chromatography on gel.

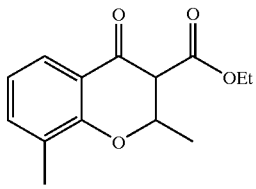

B

A solution of Part A intermediate (430 mg, 1.97 mmol) and CuI (111 mg) in 40 mL of THF was treated with MeMgBr (1.0 mL of 3.0 M in ether) at −78° C. The solution was stirred at that temperature for 1.5 h and quenched by the addition of saturated NH$_4$Cl. Standard aqueous workup and purification by flash chromatography on silica gel gave 373 mg (86%) of the desired product.

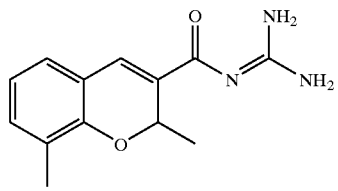

C

Sequential reduction, acid induced dehydration, and acyl guanidine formation were carried out on Part B intermediate in a similar manner to that described for Example 1 in Parts B and C.

Examples 7–14 were prepared following the method described in Example 5.

| Example | Structure | Characterization (MS) |
|---|---|---|
| 7 | 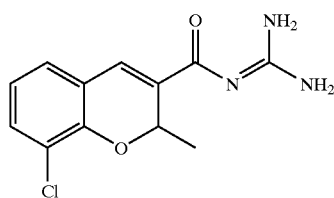 | (M+H) $^+$266 |
| 8 | 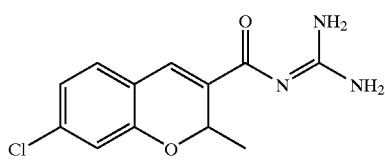 | (M+H) $^+$266 |
| 9 | 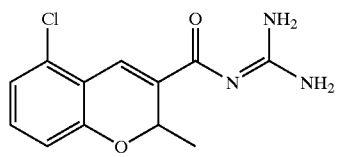 | (M+H) $^+$266 |

-continued

| Example | Structure | Characterization (MS) |
|---|---|---|
| 10 | 6-Cl, 2-Me chromene-3-carbonyl guanidine | (M+H) $^+$266 |
| 11 | 7-MeO, 2-Me chromene-3-carbonyl guanidine | (M+H) $^+$262 |
| 12 | 8-CF$_3$, 2-Me chromene-3-carbonyl guanidine | (M+H) $^+$300 |
| 13 | 5-Me, 8-OMe, 2-Me chromene-3-carbonyl guanidine | (M+H) $^+$276 |
| 14 | 8-Cl, 2-Me (Chiral) chromene-3-carbonyl guanidine | (M+H) $^+$266 |

EXAMPLE 15

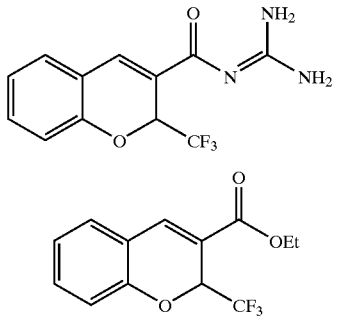

These compounds were synthesized following procedures reported in the literature (Ref: WO 9847890 A1).

A solution of Part A intermediate (0.38 g) in MeOH (9 mL) and water (1 mL) was treated with lithium hydroxide monohydrate (0.2 g) and the reaction mixture was stirred at ambient temperature overnight. It was then diluted with water and extracted with diethyl ether. The aqueous layer was separated and acidified with conc. hydrochloric acid and extracted with dichlormethane. The organic layer was separated washed with water and brine and concentrated to give the desired compound (0.3 g). This was used without further purification.

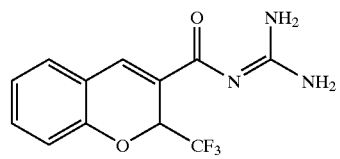

Intermediate from Part B (50 mg) was taken up in dimethylformamide (1.5 mL) and treated with carbony diimidazole (50 mg). After stirring for 2 h at ambient temperature the reaction mixture was treated with excess guanidine carbonate and the reaction mixture was stirred overnight. It was then diluted with water and extracted with ethyl acetate. The oragnic layer was separated, concentrated and the crude mixture was purifed on a preparative HPLC system using MeOH/Water/TFA as eluent to give the desired product as the TFA salt (56 mg).

Examples 16–22 were prepared following the method described in Example 15.

| Example | Structure | Characterization (MS) |
|---|---|---|
| 16 | 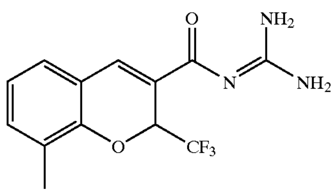 | (M+H) +294 |
| 17 | 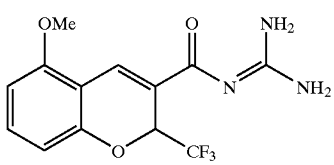 | (M+H) +316 |
| 18 | 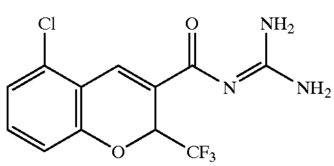 | (M+H) +320 |
| 19 | 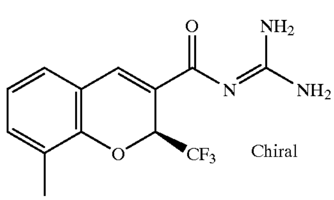 | (M+H) +294 |
| 20 | 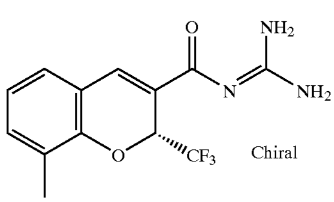 | (M+H) +294 |
| 21 | | (M+H) +320 |
| 22 | | (M+H) +320 |

EXAMPLES 23 TO 30

The following compounds may be prepared employing set out hereinbefore.

| Example | Structure |
|---|---|
| 23 | 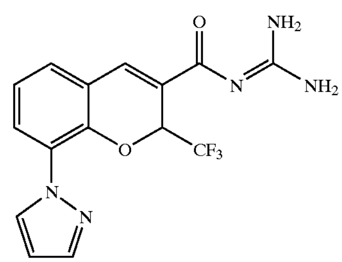 |
| 24 | 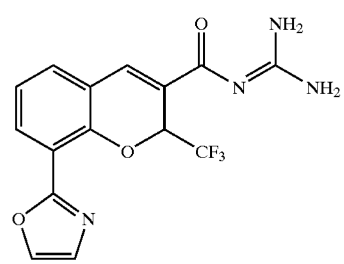 |
| 25 | 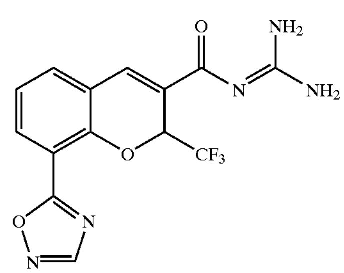 |

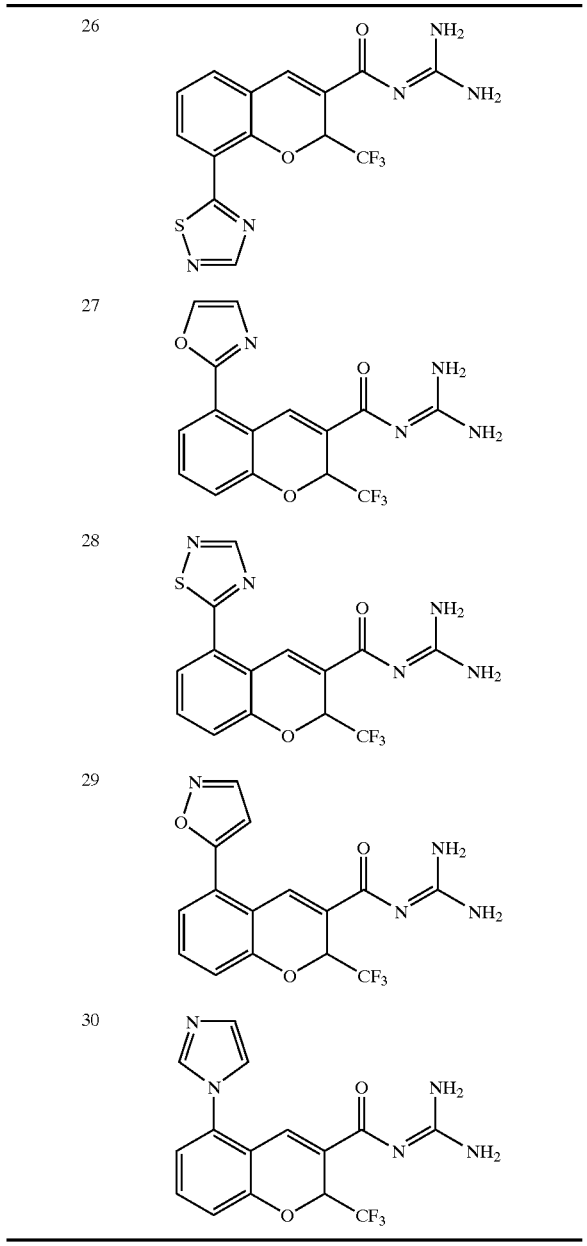

EXAMPLE 31

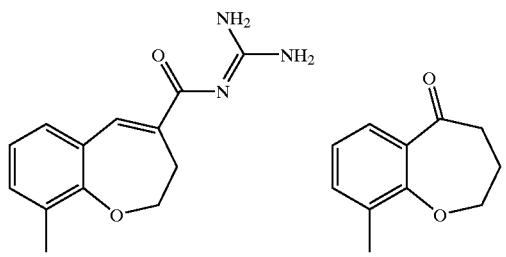

A solution containing o-cresol (1.3 g, 12 mmol) and NaH (333 mg, 13.9 mmol) in 5 mL of DMF was stirred for 10 min at rt and then methyl 4-bromobutyrate (1.5 g, 8.3 mmol) was added. The reaction was stirred for another 18 h, diluted with ethyl ether, and washed with 1N HCl. The organic layer was dried over MgSO$_4$, filtered, and concentrated. The crude residue was taken up in 20 mL of MeOH and treated with 50 mL of 1N NaOH. After stirring at rt for 1 h, the solution was diluted with water, acidified with 1N HCl, and extracted with EtOAc. The organic extracts were dried over MgSO$_4$, filtered, and concentrated under reduced pressure. This crude material was treated with 20 g of PPA and heated to 85 C for 2.5 h. After cooling to rt, the mixture was diluted with water and extracted with EtOAc. The combined organic layers were washed with 1N HCl, dried (MgSO$_4$), filtered, and concentrated under reduced pressure to yield 900 mg of the crude product.

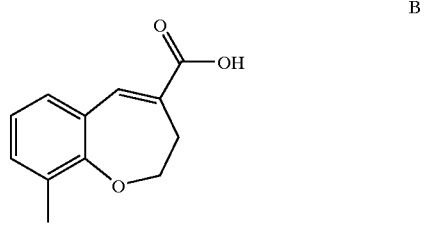

B

The crude material from part A was added to a solution of NaH (240 mg, 2 eq) in dimethyl carbonate (20 mL) and heated at 90 C for 5 h. The reaction was diluted with EtOAc and washed with 1N HCl. The organic layer was concentrated and treated with 50 mL of 1N NaOH in 50 mL of MeOH. After 1 h at rt, the solution was diluted with water, acidified with 1N HCl, and extracted with EtOAc. The combined organic layers were dried over MgSO$_4$, filtered, and concentrated under reduced pressure. The crude material was taken up in 20 mL of dioxane, treated with 10 mL of conc. HCl, and refluxed for 18 h. The solution was cooled, diluted with water, and extracted with EtOAc. The organic layers were dried over MgSO$_4$, filtered, and concentrated under reduced pressure to yield 370 mg of the desired acid.

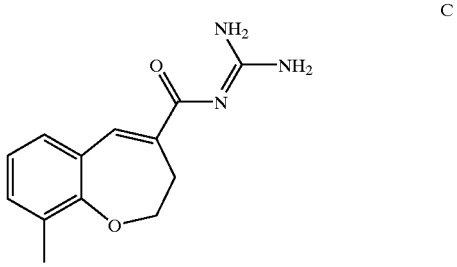

C

Conversion of the acid to the acyl guanidine was carried out in a similar manner to that described for example 15 in Part C to yield the title compound. (M+H) $^+$246.

Examples 32–34 were prepared following the method described in Example 31.

| Example | Structure | Characterization (MS) |
|---|---|---|
| 32 | benzoxepine carboxamidine | (M+H)⁺232 |
| 33 | methyl-benzoxepine carboxamidine | (M+H)⁺246 |
| 34 | methyl-benzoxepine carboxamidine | (M+H)⁺246 |

Examples 35–41 were prepared following the method described in Example 15.

| Example | Structure | Characterization (MS) |
|---|---|---|
| 35 | 5,8-dichloro-2-CF₃-chromene carboxamidine | (M+H)⁺355 |
| 36 | 5-chloro-8-methyl-2-CF₃-chromene carboxamidine | (M+H)⁺334 |
| 37 | 5-methoxy-6-fluoro-2-CF₃-chromene carboxamidine | (M+H)⁺334 |
| 38 | 5-methoxy-8-fluoro-2-CF₃-chromene carboxamidine | (M+H)⁺334 |

| Example | Structure | Characterization (MS) |
|---|---|---|
| 39 | 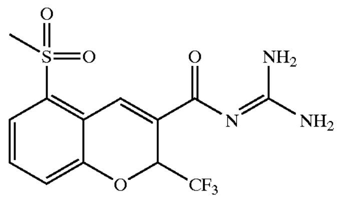 | (M+H) +364 |
| 40 | 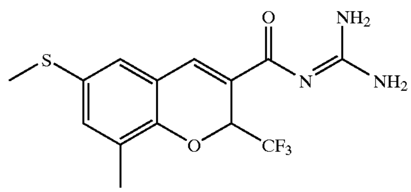 | (M+H) +346 |
| 41 | 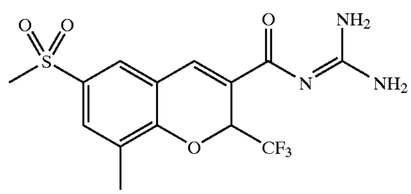 | (M+H) +378 |

What is claimed is:

1. A compound having the structure

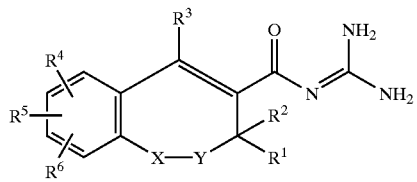

wherein

R$^1$ and R$^2$ are the same or different and are independently selected from H, alkyl, alkenyl, alkynyl, alkoxy, alkenyloxy, alkynyloxy, (alkyl or aryl)$_3$Si (where each alkyl or aryl group is independent), cycloalkyl, cycloalkenyl, aryl, arylalkyl, aryloxy, cycloheteroalkyl, cycloheteroalkylalkyl, heteroaryl, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl, polyhaloalkoxy, alkylaminocarbonyl, arylaminocarbonyl, heteroarylaminocarbonyl, acyl, carboxy, aminocarbonyl, alkylcarbonyl, alkoxycarbonyl, arylcarbonyl, heteroarylcarbonyl, cyano, tetrazolyl, imidazole, oxazole or triazole, —PO(R$^8$) (R$^9$), S(O)$_2$R$^8$, R$^9$ (where R$^8$ and R$^9$ are the same or different and are independently hydrogen, alkyl, aryl, alkoxy, aryloxy, cycloalkyl, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy);

with the proviso that when

R$^3$ is H; and

R$^4$ is H; and

R$^5$ and R$^6$ are independently H, halogen, alkyl, alkoxy, nitro, amino, aryl, cycloheteroalkyl or heteroaryl;

at least one of R$^1$ and R$^2$ is other than H;

and where R$^1$ and R$^2$ may optionally be joined together to form a non-aromatic substituted or unsubstituted carbocyclic ring, a cycloalkyl or cycloalkenyl ring, or a cycloheteroalkyl ring, which ring contains 3 to 8 members;

X is O, S, SO, S$_2$, CO, or NR$^7$ (wherein R is H, lower alkyl, alkanoyl, or —SO$_2$alkyl);

Y is a bond;

R$^3$, R$^4$, R$^5$ and R$^6$ are the same or different and are selected from H, alkyl, alkenyl, alkynyl, alkoxy, alkenyloxy, alkynyloxy, (alkyl or aryl)$_3$Si (where each alkyl or aryl group is independent), cycloalkyl, cycloalkenyl, aryl, arylalkyl, aryloxy, cycloheteroalkyl, cycloheteroalkylalkyl, heteroaryl, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl, polyhaloalkoxy, heteroarylaminocarbonyl, acyl, carboxy, aminocarbonyl, alkylcarbonyl, alkoxycarbonyl, arylcarbonyl, heteroarylcarbonyl, cyano, tetrazolyl, imidazole, oxazole or triazole, —PO(R$^{12}$) (R$^{13}$), S(O)$_2$R$^{12}$, R$^{13}$ (where R$^{12}$ and R$^{13}$ are the same or different and are independently hydrogen, alkyl, aryl, alkoxy, aryloxy, cycloalkyl, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy), amino, alkylamino, alkenylamino, alkynylamino, arylalkylamino, arylamino, heteroarylamino, thio, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, alkylcarbonyloxy, alkylcarbonylamino, arylcarbonyloxy, arylcarbonylamino, heteroarylcarbonyloxy, heteroarylcarbonylamino, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, 1,1-(alkoxyl or aryloxy)$_2$alkyl (where the two aryl or alkyl substituents can be independently defined, or linked to one another to form a ring, such as 1,3-dioxane or 1,3-dioxolane), —NR$^{10}$(C=NR$^{11}$)alkyl, —NR$^{10}$(C=NR$^{11}$)alkenyl, —NR$^{10}$(C=NR$^{11}$)alkynyl, —NR$^{10}$ (C=NR$^{11}$)heteroaryl, or —NR$^{10}$(C=NCN)-amino;

where R$^{10}$ and R$^{11}$ are the same or different and are independently selected from hydrogen, alkyl, haloaryl, aryl, alkoxy, aryloxy, cycloalkyl, heteroaryl, arylalkyl, or cycloheteroalkyl, and optionally any two adjacent R$^4$, R$^5$ and R$^6$ groups can be joined together to form a non-aromatic substituted or unsubstituted carbocyclic ring, or a cycloheteroalkyl ring or a heteroaryl ring;

including pharmaceutically acceptable salts thereof, prodrug esters thereof, and all stereoisomers thereof.

2. The compound as defined in claim 1 wherein X is O or S.

3. The compound is defined in claim 1 wherein R$^1$ and R$^2$ are the same or different and are independently selected from hydrogen, lower alkyl, perhaloalkyl, halogen, lower alkoxy or aryl, at least one of R$^1$ and R$^2$ being other than hydrogen.

4. The compound as defined in claim 1 wherein R$^3$ is H.

5. The compound as defined in claim 1 wherein R$^4$, R$^5$ and R$^6$ are the same or different and are independently selected from H, lower alkyl, lower alkoxy, aryl, perhaloalkyl or halogen.

6. The compound as defined in claim 1 wherein n is 1, X is O, R$^1$ and R$^2$ are the same or different and are independently selected from hydrogen, lower alkyl or perhaloalkyl, at least one of R$^1$ and R$^2$ being other than hydrogen; R$^3$ is H, and R$^4$, R$^5$ and R$^6$ are the same or different and are independently selected from H, lower alkyl, lower alkoxy or halogen.

7. The compound as defined in claim 1 which has the structure

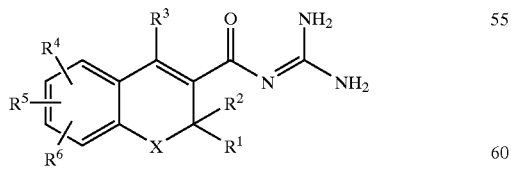

and X is O, S, SO, SO$_2$ or NR$^7$.

8. The compound as defined in claim 7 wherein X is O, either R$^1$ or R$^2$ are independently hydrogen, aryl, perhaloalkyl, or lower alkyl, at least one of R$^1$ and R$^2$ being other than hydrogen, and R$^3$ is hydrogen.

9. The compound as defined in claim 1 which is

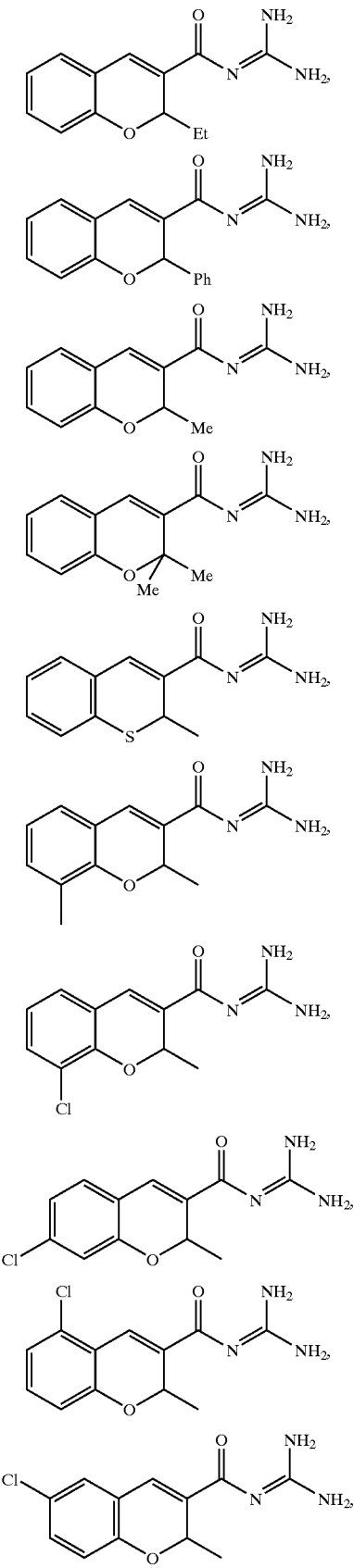

-continued
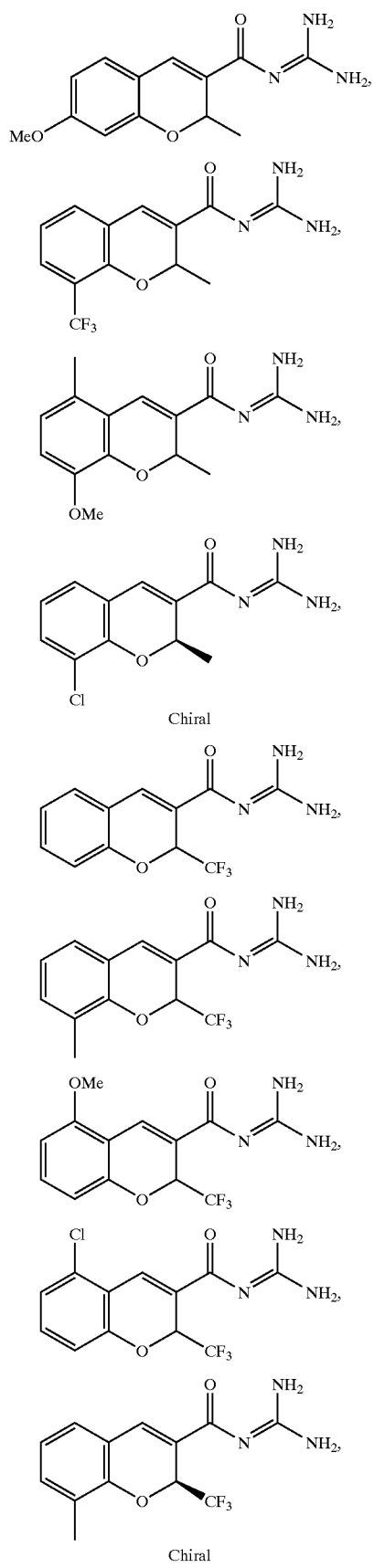
-continued
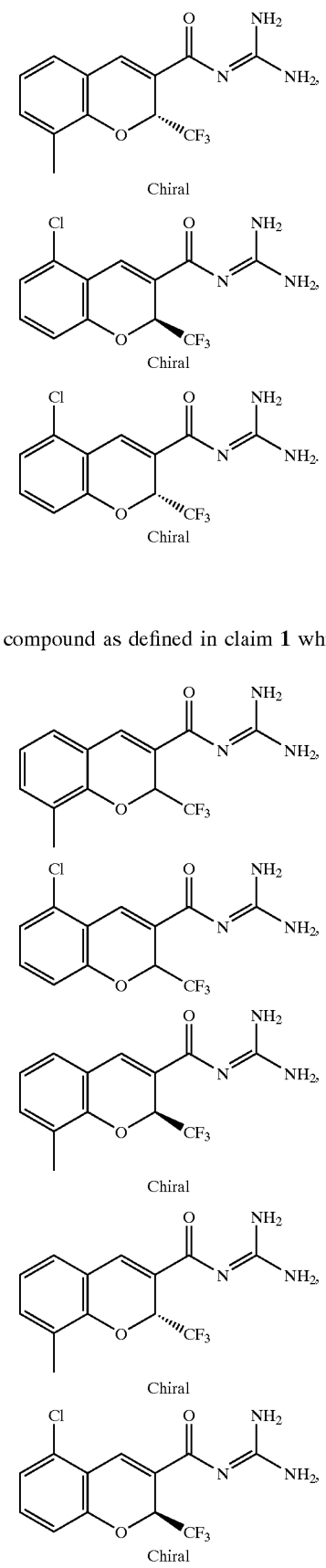
10. The compound as defined in claim 1 which is

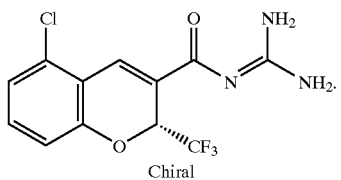
11. The compound as defined in claim 1 which is
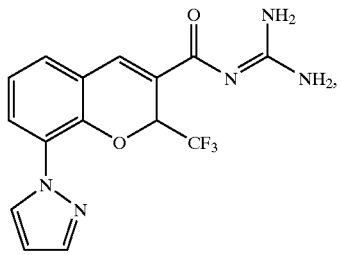
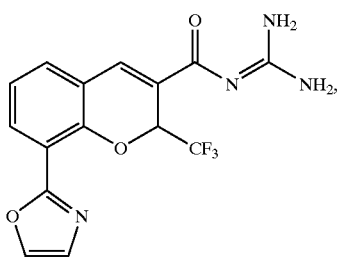
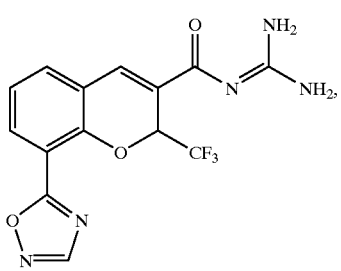
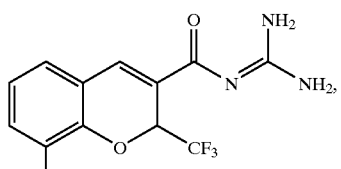
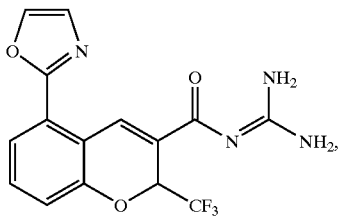
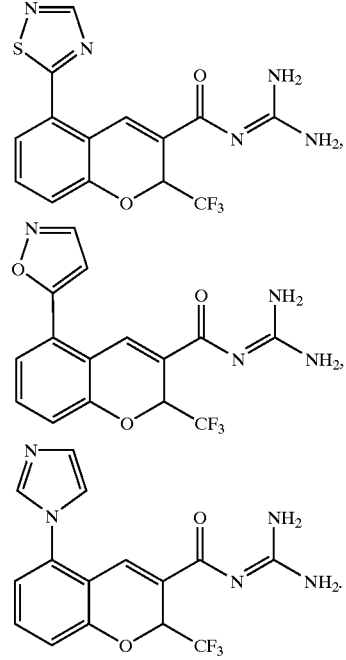
12. The compound as defined in claim 1 which is
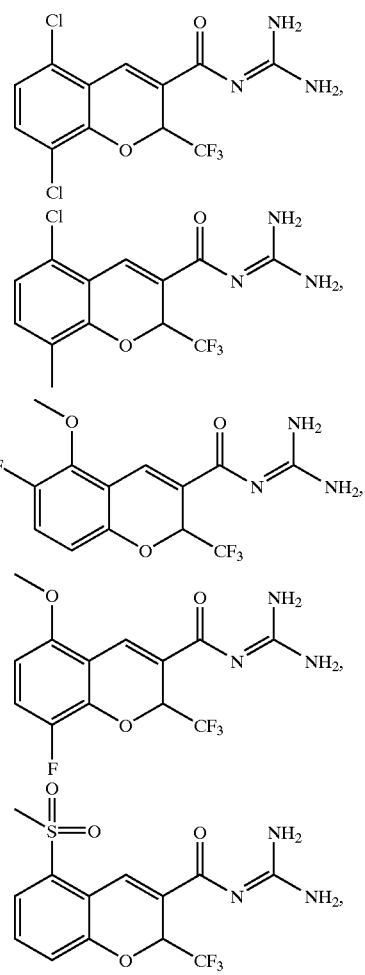

-continued

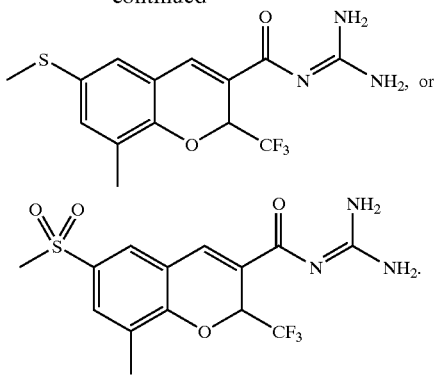

13. A pharmaceutical composition comprising a compound as defined in claim 1 and a pharmaceutically acceptable carrier therefor.

14. A method for preventing or treating disorders caused by intracellular acidosis during myocardial ischemia, hypertension, angina pectoris, cardiac arrhythmia, reperfusion injury, myocardial necrosis, cardiac dysfunction, LDL-cholesterol, renal disease or heart failure, which comprises administering to a mammalian species in need of treatment a therapeutically effective amount of a compound as defined in claim 1.

15. A method for preventing or treating myocardial ischemia, which comprises administering to a mammalian species in need of treatment a therapeutically effective amount of a compound as defined in claim 1.

16. A method for preventing or treating an ischemic condition, which comprises administering to a mammalian species in need of treatment a therapeutically effective amount of an antiischemic agent which is a compound as defined in claim 1.

17. A method for preventing or treating a peripheral vascular disorder, which comprises administering to a mammalian species in need of treatment a therapeutically effective amount of an antiischemic agent which is a compound as defined in claim 1.

18. A method for preventing or treating lower limb ischemia, which comprises administering to a mammalian species in need of treatment a therapeutically effective amount of an antiischemic agent which is a compound as defined in claim 1.

19. The method as defined in claim 16 wherein the peripheral vascular disorder is an ischemic condition.

20. The method as defined in claim 15 wherein the ischemic condition is lower limb ischemia.

21. The method as defined in claim 15 wherein the ischemic condition is peripheral atherosclerotic disease.

22. The method as defined in claim 18 wherein the peripheral atherosclerotic disease involves intermittent claudication.

23. The method as defined in claim 16 wherein the peripheral vascular disorder is Raynaud's disease or LeRiches Syndrome.

24. A method for the relief of symptoms of pain, parethesia or discomfort in the lower limb and gluteal regions produced by arterial insufficiency where symptoms are initiated or worsened with ambulation, which comprises administering to a mammalian species in need of treatment a therapeutically effective amount of a compound as defined in claim 1.

25. A method for preventing or treating intermittent claudication, which comprises administering to a patient in need of treatment a therapeutically effective amount of a compound as defined in claim 1.

26. A compound selected from

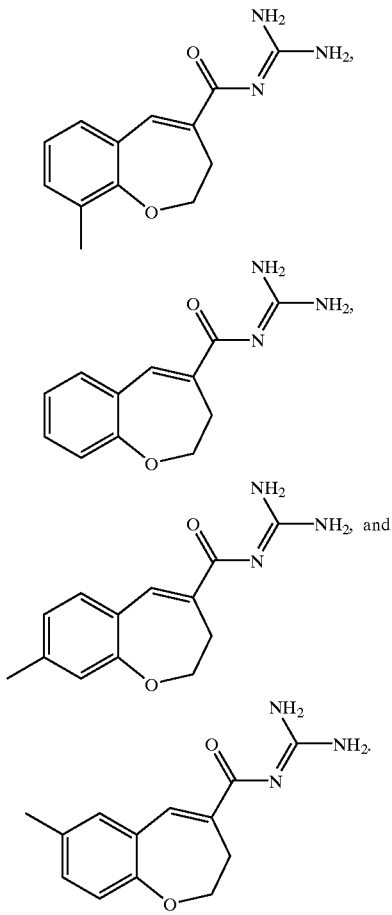

* * * * *